(12) United States Patent
Feng et al.

(10) Patent No.: US 10,932,722 B2
(45) Date of Patent: Mar. 2, 2021

(54) FLEXIBLE AND STRETCHABLE ELECTRONIC DEVICE BASED ON BIOCOMPATIBLE FILM AND PREPARATION METHOD

(71) Applicant: Tsinghua University, Beijing (CN)

(72) Inventors: Xue Feng, Beijing (CN); Ying Chen, Beijing (CN); Honghong Su, Beijing (CN); Bingwei Lu, Beijing (CN)

(73) Assignee: TSINGHUA UNIVERSITY, Beijing (CN)

(*) Notice: Subject to any disclaimer, the term of this patent is extended or adjusted under 35 U.S.C. 154(b) by 743 days.

(21) Appl. No.: 15/538,173

(22) PCT Filed: Dec. 3, 2015

(86) PCT No.: PCT/CN2015/096294
§ 371 (c)(1),
(2) Date: Jun. 20, 2017

(87) PCT Pub. No.: WO2016/101778
PCT Pub. Date: Jun. 30, 2016

(65) Prior Publication Data
US 2017/0340279 A1    Nov. 30, 2017

(30) Foreign Application Priority Data
Dec. 22, 2014   (CN) .......................... 201410811947.0

(51) Int. Cl.
*A61B 5/00* (2006.01)
*A61B 5/01* (2006.01)
(Continued)

(52) U.S. Cl.
CPC .......... *A61B 5/6833* (2013.01); *A61B 5/0024* (2013.01); *A61B 5/01* (2013.01);
(Continued)

(58) Field of Classification Search
CPC ....... A61B 5/6833; A61B 5/0024; A61B 5/01; A61B 5/02427; A61B 5/04087;
(Continued)

(56) References Cited

U.S. PATENT DOCUMENTS

| 6,855,424 | B1 | 2/2005 | Thomas et al. |
| 7,823,467 | B2 | 11/2010 | Taya et al. |

(Continued)

FOREIGN PATENT DOCUMENTS

| CN | 2427809 Y | 4/2001 |
| CN | 102387746 A | 3/2012 |

(Continued)

OTHER PUBLICATIONS

Li, Zhou, A New Covering Material of Skin for Burned Surgery, China Academic Journal Electronic Publishing House, 1994; 11(3).
(Continued)

*Primary Examiner* — Aaron F Roane
(74) *Attorney, Agent, or Firm* — Holzer Patel Drennan

(57) ABSTRACT

Disclosed is a flexible and stretchable electronic device based on a biocompatible film. The biocompatible film is utilized as an encapsulation layer and a substrate layer of the device; a bonding layer is provided between the encapsulation layer and a functional layer; and an adhesion layer is arranged under the substrate layer. The functional layer employs a flexible and stretchable structure. Solution-based transfer printing technology is primarily used during the preparation of such a device to achieve integration of the functional layer and the flexible substrate layer. This device retains and even enhances the flexibility and stretchability structurally. Meanwhile, the biocompatibility properties thereof, such as being waterproof and air permeable, hypoallergenic, etc., allow it to work normally on the human body surface for more than 24 hours without foreign body sen- (Continued)

sation and discomfort, and thus, skin maceration, redness or other allergic reactions due to poor biocompatibility can be avoided.

7 Claims, 3 Drawing Sheets

(51) Int. Cl.
*H05K 1/02* (2006.01)
*H05K 1/11* (2006.01)
*A61B 5/024* (2006.01)
*A61B 5/0408* (2006.01)

(52) U.S. Cl.
CPC ....... *A61B 5/02427* (2013.01); *H05K 1/0283* (2013.01); *H05K 1/118* (2013.01); *A61B 5/04087* (2013.01); *A61B 2562/12* (2013.01); *H05K 2201/0116* (2013.01); *H05K 2201/0133* (2013.01); *H05K 2201/09263* (2013.01)

(58) Field of Classification Search
CPC .. A61B 2562/12; H05K 1/0283; H05K 1/118; H05K 2201/0116; H05K 2201/0133; H05K 2201/09263
USPC ........................................................ 600/301
See application file for complete search history.

(56) References Cited

U.S. PATENT DOCUMENTS

| | | |
|---|---|---|
| 2009/0012380 A1 | 1/2009 | Gonopolski et al. |
| 2011/0208071 A1 | 8/2011 | Lu et al. |
| 2012/0296444 A1* | 11/2012 | Greenberg ........... A61N 1/0534 623/25 |
| 2013/0297019 A1 | 11/2013 | Tai et al. |

FOREIGN PATENT DOCUMENTS

| | | |
|---|---|---|
| CN | 102804333 A | 11/2012 |
| CN | 102883970 A | 1/2013 |
| CN | 103282303 A | 9/2013 |
| CN | 103872002 A | 6/2014 |
| CN | 104523227 A | 4/2015 |
| JP | 0852816 A | 2/1996 |

OTHER PUBLICATIONS

Office Action, SIPO, dated Dec. 20, 2016 Application No. 201410811947.0.

Office Action, SIPO, dated Apr. 28, 2016, Application No. 20140811947.0.

* cited by examiner

FLEXIBLE AND STRETCHABLE ELECTRONIC DEVICE BASED ON BIOCOMPATIBLE FILM AND PREPARATION METHOD

CROSS-REFERENCE TO RELATED APPLICATIONS

The present application is a national phase entry of PCT Patent Application No. PCT/CN2015/09624, entitled "FLEXIBLE EXTENSILE ELECTRONIC DEVICE BASED ON BIOCOMPATIBLE FILM AND PREPARATION METHOD" and filed on 3 Dec. 2015. The present application further claims priority to Chinese Patent Application No 201410811974.0, entitled "FLEXIBLE EXTENSILE ELECTRONIC DEVICE BASED ON BIOCOMPATIBLE FILM AND PREPARATION METHOD", and filed on 22 Dec. 2014, both of which are specifically incorporated by reference herein for all that they disclose or teach.

TECHNICAL FIELD

The present invention relates to a flexible and stretchable electronic device based on a biocompatible film and a method for preparing the same, which is applicable but not limited to various vital sign sensors.

BACKGROUND

In medical care and health monitoring, a variety of sensors is typically required to monitor the physiological information of human body intermittently or in real time, and conventional measurements comprise body temperature, pulse rate, heart rate, ECG, blood oxygen and other signals. At present, whether in clinic or health care consumer electronics, the devices for testing the corresponding signals, such as mercury thermometer, hand hold pulse oximeter, ECG electrode and so on, adopt a hard-to-soft contact type. They all employ reliable and effective principles of physical chemistry. However, there are some unavoidable problems with the hard-to-soft contact: the discomfort caused by hard contact to the patient may affect the performance of normal physiological parameters; the mismatch of hard contact will make the detection signal be affected by the contact extent; and 24-hour comfortable and effective health monitoring cannot be achieved by means of such equipments. Therefore, the research on electronic components/elements integratable with human body, as a large branch of flexible electronics, has a wide range of civil business value.

Since "Science" reported a study on the skin electronics in 2011, the electronic components integratable with epidermis of human body aroused the research interest of numerous research workers, and various flexible sensors capable of measuring moisture, body temperature, ECG, EMG or other human physiological signals emerged in succession. The sensors use thin and flexible polymer film material as a substrate to enable the flexible functional devices to contact with human skin directly or indirectly by using a bonding layer or Van der Waals force, thereby acquiring a variety of physiological signals on the skin surface. The above researches focus on how devices can achieve flexibility and stretchability, and lack the consideration of biocompatibility of devices on human body surface over long periods. The flexible devices using Van der Waals force to adhere have poor adhesion to hairy skin. The flexible devices using a bonding layer to adhere are difficult to be kept on the skin surface of the human body for a long time due to lack of breathability.

SUMMARY

It is an object of the present invention to provide a flexible and stretchable electronic device based on a biocompatible film and a method for preparing the same to solve the problem of biocompatibility when the flexible and stretchable electronic device is combined with the human body. The flexible and stretchable electronic device based on the biocompatible film has the following properties, comprising, but not limited to, ① biocompatibility: the device does not chemically contain chemical compositions which are harmful to the human body, and the device has air permeability physically, so that the sweat on the body surface can evaporate normally, thereby avoiding maceration or allergic reaction; and ② flexibility and stretchability: flexibility requires that the bending stiffness of the device (comprising the substrate layer and the functional layer) is small so that the device can be flexibly bent to be adapt to the natural curvature of the surface of the human tissue, and stretchability requires that the tensile stiffness of the device is small so that the device can be deformed in the in-plane direction to be adapt to the non-developable surface of the human tissue.

The technical solutions of the present invention are described below.

A flexible and stretchable electronic device based on a biocompatible film comprises an encapsulation layer, a functional layer and a substrate layer, wherein the encapsulation layer employs a biocompatible encapsulation layer, and the substrate layer employs a biocompatible substrate layer. The biocompatible encapsulation layer and the biocompatible substrate layer each employs a biocompatible film.

The technique of the present invention is also characterized in that a bonding layer is provided between the biocompatible encapsulation layer and the functional layer, and the bonding layer is used for enhancing an interfacial strength between the biocompatible encapsulation layer and the functional layer. An adhesion layer is provided under the biocompatible substrate layer, and the adhesion layer is used for enhancing an adhesive force between the device and a surface of an object to be detected.

The biocompatible film of the present invention is a polymer film or a biologic semi-permeable membrane featuring with porous microstructures. The thickness of the biocompatible encapsulation layer is the same as the thickness of the biocompatible substrate layer.

The functional layer of the present invention comprises a functional element, an interconnection wire, and an extraction electrode. The functional element employs a material having thermo-resistive effect, piezoresistive effect, or piezoelectric effect.

The functional layer of the present invention employs a flexible and stretchable structure. The flexible and stretchable structure preferably employs an island-bridge structure, an S-shaped structure or a wavy buckling structure.

The present invention provides a method for preparing a flexible and stretchable electronic device based on a biocompatible film, wherein the method comprises the following steps:

1) preparing a sacrificial layer on a silicon wafer;
2) growing and preparing a functional layer material on the silicon wafer using film growth technique;

3) forming a functional layer by performing lithography and etching on the functional layer material using semiconductor technology and completing patterning;

4) bonding a biocompatible film to the functional layer on the silicon wafer;

5) putting the biocompatible film and the silicon wafer with the functional layer together into an etching solution for the sacrificial layer and etching the sacrificial layer, so as to form a combination of a biocompatible substrate layer (5) and the functional layer;

6) connecting outer connecting wires to the extraction electrodes reserved in the functional layer;

7) encapsulating the device using a biocompatible film and forming a biocompatible encapsulation layer, so as to complete the preparation of the device.

In the method of the present invention, wherein in the steps 4) to 5), the functional layer is integrated with the biocompatible substrate layer by using transfer printing technique.

Compared with the conventional flexible and stretchable electronic device, the present invention has the following advantages and high-lighting technical effects: the device fabricated using the method of the present invention employs a biocompatible encapsulation layer and a stretchable biocompatible substrate layer to introduce good biocompatibility for conventional flexible and stretchable electronic device while maintaining or even enhancing the flexibility and stretchability thereof. Meanwhile, the biocompatibility properties of the device, such as being waterproof and air permeable, hypoallergenic, etc., allow the device to work normally on the human body surface for more than 24 hours, without foreign body sensation and discomfort, and thus, skin maceration, redness or other allergic reactions due to poor biocompatibility (airtight) can be avoided.

Figure 1:
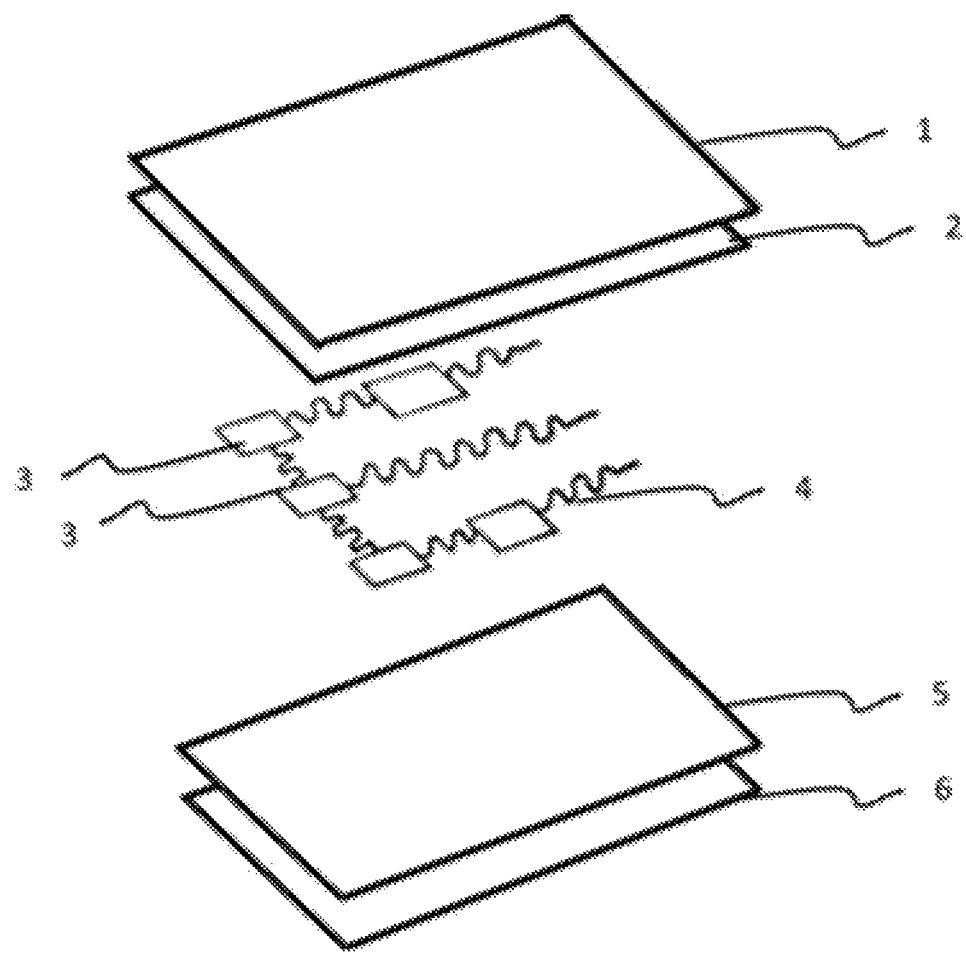
FIG. 1 is a schematic view of a layered three-dimensional structure of a flexible and stretchable electronic device based on a biocompatible film according to the present invention.

In the drawings: 1—biocompatible encapsulation layer; 2—bonding layer; 3—functional element; 4—interconnection wire; 5—biocompatible substrate layer; 6—adhesion layer; 7—functional layer.

DETAILED DESCRIPTION

The details of the present invention will be further described below with reference to the accompanying drawings and embodiments.

Figure 2:
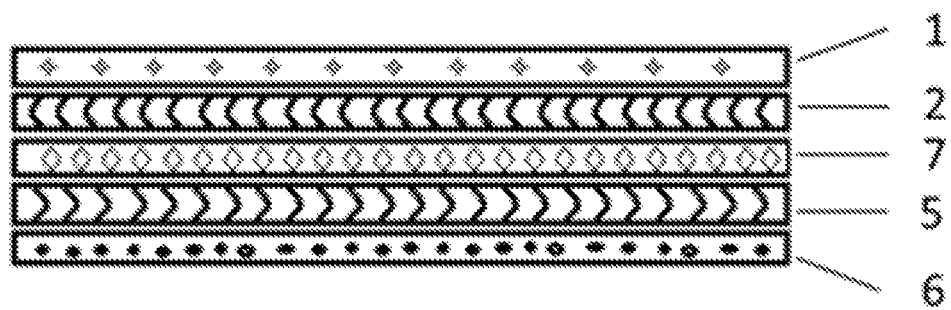
FIG. 2 is a layered schematic sectional view of a flexible and stretchable electronic device based on a biocompatible film according to the present invention.

FIG. 1 and FIG. 2 show a layered three-dimensional structure and a layered schematic sectional view of a flexible and stretchable electronic device based on a biocompatible film provided by the present invention. The basic structure of the flexible and stretchable electronic device is the biocompatible encapsulation layer/the functional layer/the biocompatible substrate layer, wherein the biocompatible encapsulation layer 1 is a kind of film having biocompatibility, comprising but not limited to, polymer film having porous microstructure (e.g., porous polyurethane film) or biologic semi-permeable membrane (e.g., biological tissue film with selective permeability), and has a thickness of several tens of microns, and the main feature is that the non-penetrating holes having diameters ranging from hundreds of nanometers to tens of microns are distributed on the film, oxygen and water vapor can pass through the holes, but liquid water and bacteria cannot pass through the holes. Therefore, such kind of film has biocompatibility, waterproof and breathable function, and has good biocompatibility when applied to human body surface.

The biocompatible substrate layer 5 is also made of a film having biocompatibility described above for supporting the functional element 3 and the interconnection wire 4. Each of the functional element 3 and the interconnection wire 4 is designed to have flexibility and stretchability, the non-stretchable functional element 3 may be provided with a buffer layer to isolate strain, and the stretchability of the interconnection wire 4 is achieved through an S-shaped fractal design. The wire with the S-shaped fractal design is adapted to the tensile deformation in the substrate surface by increasing the wavelength and reducing the amplitude in the in-plane direction.

The biocompatible film is used as the flexible substrate layer, so as to utilize the air permeability, water resistance, and low sensitization of the biocompatible film to provide the biocompatibility for the entire device, so that the device can operate on the human tissue (comprising but not limited to, the skin) surface more than 24 hours. An integrated functional layer of the device is provided on the biocompatible substrate layer 5, and the functional layer comprises various functional elements 3, interconnection wires 4, and extraction electrodes. Each type of functional elements 3 and their interconnection wires 4 are designed to have a flexible and stretchable structure, such as an island bridge structure, a buckling structure or an in-plane bending structure. The biocompatible encapsulation layer 1 is used for encapsulating to protect the structural integrity of the functional device, and prevent the circuit function and biocompatibility from being destroyed by external liquid. The device may be integrally encapsulated, or only parts of the device where the functional elements 3 and the interconnection wires 4 exist may be locally encapsulated.

The device is finally encapsulated with a biocompatible encapsulation layer 1 having the same thickness as the biocompatible substrate layer 5. Thus, the biocompatibility of the entire device can be ensured, and the functional elements 3 and the interconnection wires 4 in the device can be located in the mechanical neutral layer of the entire structure, so as to reduce the stress and strain acting on the functional elements 3 under bending deformation load.

A bonding layer 2 is selectively provided between the biocompatible encapsulation layer 1 and the functional layer, and has a thickness of about several microns. If both the biocompatible encapsulation layer 1 and the functional layer are thin enough, the biocompatible encapsulation layer 1 and the functional layer can be bonded with each other by using Van der Waals force without the bonding layer 2. An adhesion layer 6 is selectively provided between the biocompatible substrate layer 5 and the surface (human skin) of the object to be detected for enhancing the adhesive force between the device and the surface of the object to be detected. The adhesion layer is formed by a material with strong viscosity and very low sensitization, which enables the entire device to securely contact with the human tissue surface and be less prone to debond.

The element in the functional layer may be a temperature sensing member utilizing thermo-resistive effect of the metal, a strain sensing member utilizing piezoresistive effect of the semiconductor or metal, or an energy harvesting member utilizing piezoelectric effect of the piezoelectric material, etc. Different functional materials and structural forms may achieve different types of signal acquisition functions. The elements of the biocompatible flexible and stretchable electronic device with a single function or multiple functions may be prepared using the preparing process shown in FIG. 3.

Figure 3:
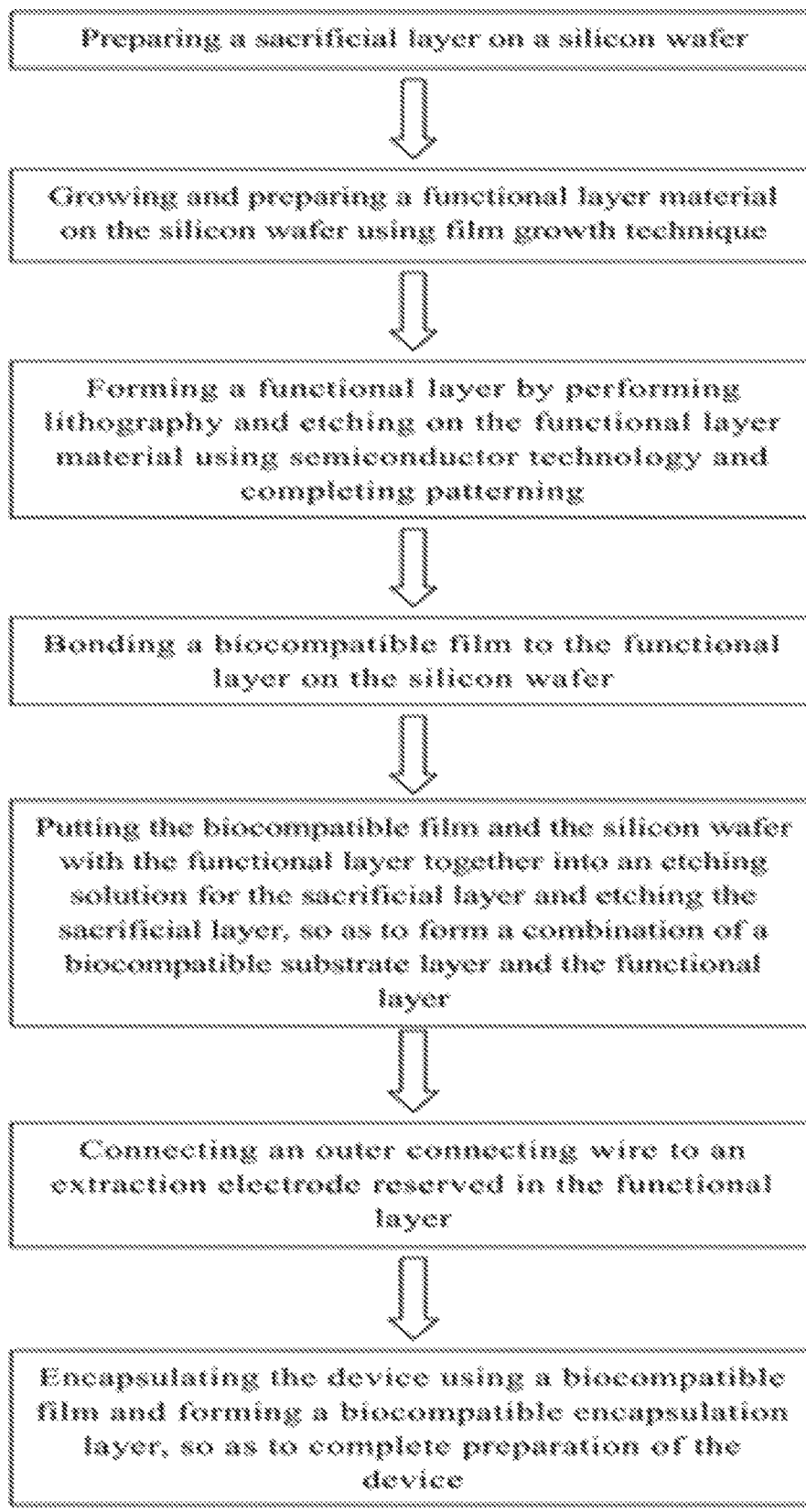
FIG. 3 is a process of the preparation process based on transfer printing according to the present invention.

FIG. 3 is a process flow diagram of a method for preparing a flexible and stretchable electronic device based on a biocompatible film according to the present invention, and the method comprises the following steps:

1) preparing a sacrificial layer on a silicon wafer;

2) growing and preparing a functional layer material on the silicon wafer using film growth technique;

3) forming a functional layer by performing lithography and etching on the functional layer material using semiconductor technology and completing patterning;

4) bonding a biocompatible film to the functional layer on the silicon wafer;

5) putting the biocompatible film and the silicon wafer with the functional layer into an etching solution for the sacrificial layer and etching the sacrificial layer, so as to form a combination of the biocompatible substrate layer 5 and the functional layer;

6) connecting an outer connecting wire to an extraction electrode reserved in the functional layer;

7) encapsulating the device using a biocompatible film and forming a biocompatible encapsulation layer 1, so as to complete the preparation of the device.

In the above method for preparation, the steps 2) to 3) may be repeated if required according to the functional design requirements on different devices, so as to prepare a plurality of layers, and insulating layers are used for isolating respective layers, or the respective layers are perforated to facilitate connection. In the step 4) (transfer print), the biocompatible film may be bonded to the functional layer on the silicon wafer through the bonding layer 2, and then the biocompatible film and the silicon wafer may be put into the etching solution for the sacrificial layer to etch the sacrificial layer, thereby completing the process for transferring the functional layer to the flexible substrate layer. Also, a transfer stamp with a novel microstructure may be used for integrating the functional layer with the flexible substrate layer without using the bonding layer 2. In step the 6), in order to achieve well contact between the flexible device and the skin, a layer of adhesion layer 6 may be used for reinforcing the bonding between the skin and the biocompatible substrate layer 5. If the thickness of the device is small enough, the adhesion layer 6 is not used, and the device and the skin are securely bonded to each other under Van der Waals force directly.

In the above method, a biocompatible film is used as the biocompatible substrate layer 5, the functional layer is prepared on the silicon wafer by using traditional semiconductor technology, film growth technique, lithography technology and the like, and a biocompatible film is used as a biocompatible encapsulation layer 1 on the top. Adhesive with lower sensitization, which is used as the bonding layer 2 and the adhesion layer 6, is applied between the functional layer and the biocompatible encapsulation layer 1, and between the biocompatible substrate layer 5 and the surface of the object to be detected. The integration of the functional layer with the biocompatible substrate layer 5 may be achieved by the transfer printing method during preparation.

In the preparation process, the integration of the functional layer with the biocompatible substrate layer 5 is achieved by the transfer printing method. The functional layer is prepared on the silicon wafer using conventional semiconductor processes, comprising film growth, lithography, etching, and the like. A sacrificial layer is prepared in advance on the silicon wafer to facilitate stripping of the functional layer from the silicon wafer, and facilitate transfer printing. Requirements to be met in selection of materials and preparation processes of the sacrificial layer: 1) capable of ensuring smooth completion of functional layer preparation, that is, the sacrificial layer has a flatness, hardness and glass transition temperature which meet the requirements on the film growth conditions of the functional part, and do not affect the film growth quality; 2) capable of ensuring smooth completion of patterning etching of the functional part, that is, the sacrificial layer can withstand physical and chemical reactions in the lithography process and etching process, and may not be vitrified; and 3) after the preparation of the functional layer is completed, the sacrificial layer can be easily etched, and the reaction does not affect the pattern and the material properties of the functional part.

A particular embodiment is described as follows.

Embodiment 1: A flexible and stretchable temperature sensor based on a biocompatible film.

This embodiment provides a stretchable electronic device based on a biocompatible film utilizing the thermo-resistive effect of gold. The device is made by adopting the design method and preparation flow provided in the technical solutions of the present invention, wherein each of the biocompatible encapsulation layer 1 and the biocompatible substrate layer 5 is made of a porous polyurethane film with a thickness of 50 μm, the bonding layer 2 and the adhesion layer 6 are made of acrylic acid with low sensitization and high viscosity, and the functional elements 3 and interconnection wires 4 in the functional layer are patterned gold nanofilms. The device can be used for measuring body temperature. The method for preparing the device is described as follows.

1) Firstly, a flat sacrificial layer is prepared on the silicon wafer, that is, a layer of PI film is prepared on the silicon wafer by using spin coating, and then horizontally placed to be dried to form the sacrificial layer.

2) A layer of dense and flat chromium is formed by using electron beam deposition to form a metal bonding layer, and then a layer of gold as a functional layer material having thermo-resistive effect is formed on the metal bonding layer. The chromium bonding layer binds the gold to the substrate more closely. During the electron beam deposition, as the wafer suffers from smaller temperature rise, the soluble polymer in the sacrificial layer will not be vitrified to become insoluble, thereby ensuring that the sacrificial layer is easy to be etched in the subsequent process so as to release the functional parts from the silicon wafer.

3) By using conventional semiconductor micromachining technology, such as lithography and wet etching, the gold/chromium film is patterned into a flexible and stretchable pattern, thereby forming the functional elements 3 having thermo-resistive effect and the interconnection wires 4 in the sensor to form the functional layer.

4) The photoresist left on the surface is removed, and then a biocompatible film is flattened and bonded to the prepared silicon wafer with functional parts, and ready for transfer printing. Transfer printing is a technique in which a functional layer prepared by a conventional semiconductor process is peeled from a silicon wafer and printed onto a flexible substrate for a flexible electronic device, whereby the integration of the functional layer with the biocompatible substrate layer 5 may be achieved.

5) The sacrificial layer is etched by using the etching solution. As the etching is completed, the functional layer is fully released from the silicon wafer and integrated integrally to the biocompatible substrate layer 5.

6) Finally, the exposed parts of the device are encapsulated with a porous polyurethane film having the same thickness to form the biocompatible encapsulation layer 1. The encapsulation is used for protecting the functional parts, while enables the functional layer to be located at the neutral layer of the final device.

What is claimed is:

1. A flexible and stretchable electronic device, configured to be applied to a human body external surface, comprising:
    an encapsulation layer;
    a substrate layer: and
    an electronic functional layer encapsulated between the encapsulation layer and the substrate layer;
    wherein the encapsulation layer employs a biocompatible encapsulation layer, the substrate layer employs a biocompatible substrate layer, and the biocompatible encapsulation layer and the biocompatible substrate layer each employ a biocompatible film, wherein the biocompatible film is a polymer film that is breathable and waterproof having a porous microstructure with holes having diameters ranging from hundreds of nanometers to tens of microns.

2. The flexible and stretchable electronic device according to claim 1, wherein a bonding layer is provided between the biocompatible encapsulation layer and the electronic functional layer, and the bonding layer is used for enhancing an interfacial strength between the biocompatible encapsulation layer and the electronic functional layer.

3. The flexible and stretchable electronic device according to claim 1, wherein an adhesion layer is provided on the biocompatible substrate layer on a side opposite the electronic functional layer, and the adhesion layer is used for enhancing an adhesive force between the device and the human body external surface.

4. The flexible and stretchable electronic device according to claim 1, wherein a thickness of the biocompatible encapsulation layer is equal to a thickness of the biocompatible substrate layer.

5. The flexible and stretchable electronic device according to claim 1, wherein the electronic functional layer employs a flexible and stretchable structure.

6. The flexible and stretchable electronic device according to claim 5, wherein the flexible and stretchable structure employs one of an island-bridge structure, an S-shaped structure, and a wavy buckling structure.

7. The flexible and stretchable electronic device according to claim 1, wherein the electronic functional layer comprises a functional element, an interconnection wire, and an extraction electrode, and the functional element employs a material having one of a thermo-resistive effect, a piezoresistive effect, and a piezoelectric effect.

* * * * *